US008285734B2

(12) United States Patent
Baras et al.

(10) Patent No.: US 8,285,734 B2
(45) Date of Patent: Oct. 9, 2012

(54) COMPARISON OF DOCUMENTS BASED ON SIMILARITY MEASURES

(75) Inventors: Dorit Baras, Ashdod (IL); Ohad Moti Greenshpan, Ra'anana (IL); Amnon Shabo, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 353 days.

(21) Appl. No.: 12/260,215

(22) Filed: Oct. 29, 2008

(65) Prior Publication Data

US 2010/0104200 A1 Apr. 29, 2010

(51) Int. Cl.
*G06F 7/00* (2006.01)
*G06F 17/30* (2006.01)
(52) U.S. Cl. ........................ 707/758; 707/780
(58) Field of Classification Search ............ 707/999.004
See application file for complete search history.

(56) References Cited

U.S. PATENT DOCUMENTS

| | | | |
|---|---|---|---|
| 6,286,000 B1* | 9/2001 | Apte et al. ............................. | 1/1 |
| 6,542,173 B1* | 4/2003 | Buckley ........................ | 715/841 |
| 7,254,587 B2* | 8/2007 | Lee et al. ................................ | 1/1 |
| 7,752,204 B2* | 7/2010 | Kao et al. ........................ | 707/736 |
| 2004/0122709 A1 | 6/2004 | Avinash et al. | |
| 2005/0021517 A1* | 1/2005 | Marchisio ........................ | 707/4 |
| 2007/0118518 A1* | 5/2007 | Wu et al. ............................ | 707/5 |
| 2007/0239707 A1* | 10/2007 | Collins et al. ..................... | 707/5 |
| 2007/0299697 A1 | 12/2007 | Friedlander et al. | |
| 2008/0270437 A1* | 10/2008 | Kahn et al. ..................... | 707/101 |
| 2009/0125529 A1* | 5/2009 | Vydiswaran et al. ......... | 707/100 |
| 2009/0240687 A1* | 9/2009 | Eskebaek .......................... | 707/5 |

FOREIGN PATENT DOCUMENTS

WO WO2008056128 5/2008

OTHER PUBLICATIONS

WIPO Publication WO/2008/012279, Published Jan. 31, 2008.*
M. Watson et al., "Leximancer Concept Mapping of Patient Case Studies," 2005, Knowledge-Based Intelligent Information and Engineering Systems, 9th International Conference, pp. 1232-1238.
J.H. Yun et al., "Processing HL7-CDA Entry for Semantic Interoperability," International Conference on Convergence Information Technology, 2007, pp. 1939-1944.

* cited by examiner

*Primary Examiner* — Jay Morrison
(74) *Attorney, Agent, or Firm* — Ryan, Mason & Lewis, LLP

(57) ABSTRACT

Techniques for comparing a first document to one or more second documents are provided. At least one weight is assigned to one or more elements in the first document. A weighted document is generated in accordance with the at least one assigned weight. One or more comparison scores are computed by comparing each of the one or more elements in the first document to each of one or more elements in a given second document in accordance with one or more comparison rules. The one or more comparison rules determine if a given element in the first document and a given element in the given second document are compared using one or more language hierarchies and/or one or more similarity ranges. A similarity score is generated in accordance with the generated weighted document and the one or more computed comparison scores. The one or more second documents are retrieved in accordance with the generated similarity score.

22 Claims, 3 Drawing Sheets

COMPARISON OF DOCUMENTS BASED ON SIMILARITY MEASURES

FIELD OF THE INVENTION

The present invention relates generally to document analysis and, particularly, to techniques for comparing documents using one or more similarity measures.

BACKGROUND OF THE INVENTION

Document analysis and retrieval has become exceedingly difficult due to a large number of available documents and a lack of uniformity in the way in which documents are prepared. Even if a set of documents conform to a standard document format, there may still be difficulty in comparing those documents to each other because document preparers may use different words and/or terminology during document preparation. This may be the case in specialized documents such as, for example, clinical documents using Health Level 7 (HL7) Clinical Document Architecture (CDA).

Clinical documents typically summarize care and services given to a patient and health conditions of that patient. For instance, a discharge summary may summarize a specific hospitalization event and a report note may summarize a surgery a patient has undergone. Considering the large number and numerous types of clinical documents available, a practitioner can not efficiently compare one clinical document to a database of clinical documents. Under conventional techniques, if a practitioner is interested in comparing a given clinical document to a database of clinical documents the practitioner must either: (1) manually and systematically compare the clinical documents of his/her patient to a large database of clinical cases, which is unrealistic; and/or (2) rely on conventional document comparison techniques.

Conventional techniques inefficiently evaluate documents because they simply compare text strings (e.g., basic keyword search). Searching for documents by keyword may be especially ineffective when analyzing medical documents because medical practitioners may use different words and/or terms to describe similar events. As a result, conventional comparison systems may not recognize a relationship between two documents, which use different words but are substantively the same. For example, generic medications which are based on the same drug formula may have different names. Another example includes the names of diseases. A disease like Hepatitis B may be written as initials (i.e., "HBV"), a full name (i.e., "Hepatitis B Virus"), and/or any other variation (e.g., "Hep B"). Additionally, beyond the precise identification of a term (e.g., medication, disease, symptom, etc.), conventional techniques are unable to measure the overall similarity between two documents.

SUMMARY OF THE INVENTION

Principles of the present invention provide techniques that overcome the above-mentioned drawbacks associated with existing methods by providing techniques that address the above needs, as well as other needs. Particularly, principles of the invention provide techniques for comparing documents using one or more defined weights.

For example, in one embodiment of the invention, a technique for comparing a first document to one or more second documents is provided. At least one weight is assigned to one or more elements in the first document. A weighted document is generated in accordance with the at least one assigned weight. One or more comparison scores are computed by comparing each of the one or more elements in the first document to each of one or more elements in a given second document in accordance with one or more comparison rules. The one or more comparison rules determine if a given element in the first document and a given element in the given second document are compared using one or more language hierarchies and/or one or more similarity ranges. A similarity score is generated in accordance with the generated weighted document and the one or more computed comparison scores. The one or more second documents are retrieved in accordance with the generated similarity score.

In additional embodiments, the above technique for comparing a first document to one or more second documents may be carried out by an apparatus, a computer program product, and/or a system comprising one or more components.

These and other objects, features, and advantages of the present invention will become apparent from the following detailed description of illustrative embodiments thereof, which is to be read in connection with the accompanying drawings.

DETAILED DESCRIPTION OF PREFERRED EMBODIMENTS

The present invention will be described in conjunction with exemplary methods for comparing a first document to one or more second documents. Specifically, the present disclosure will illustrate comparing a medical document in CDA format to a database of medical documents in CDA format. It should be understood, however, that the invention is not limited to the particular embodiments described herein. For instance, the disclosed comparison techniques may be applied to any document of any format, not only medical documents in CDA format. Modifications to the illustrative embodiments will become apparent to those skilled in the art given the teachings described herein.

Conventional techniques are ill-equipped to compare documents at a substantive level. For instance, conventional techniques cannot handle a comparison of various words and/or terms that may have the same meanings. Further, conventional techniques do not retrieve documents using a meaningful measure of similarity. For example, two documents may contain the same general terms (e.g., words, numbers, etc.); however, unless the comparison can weigh the importance of each term, an irrelevant document may be incorrectly deemed similar.

Figure 1:
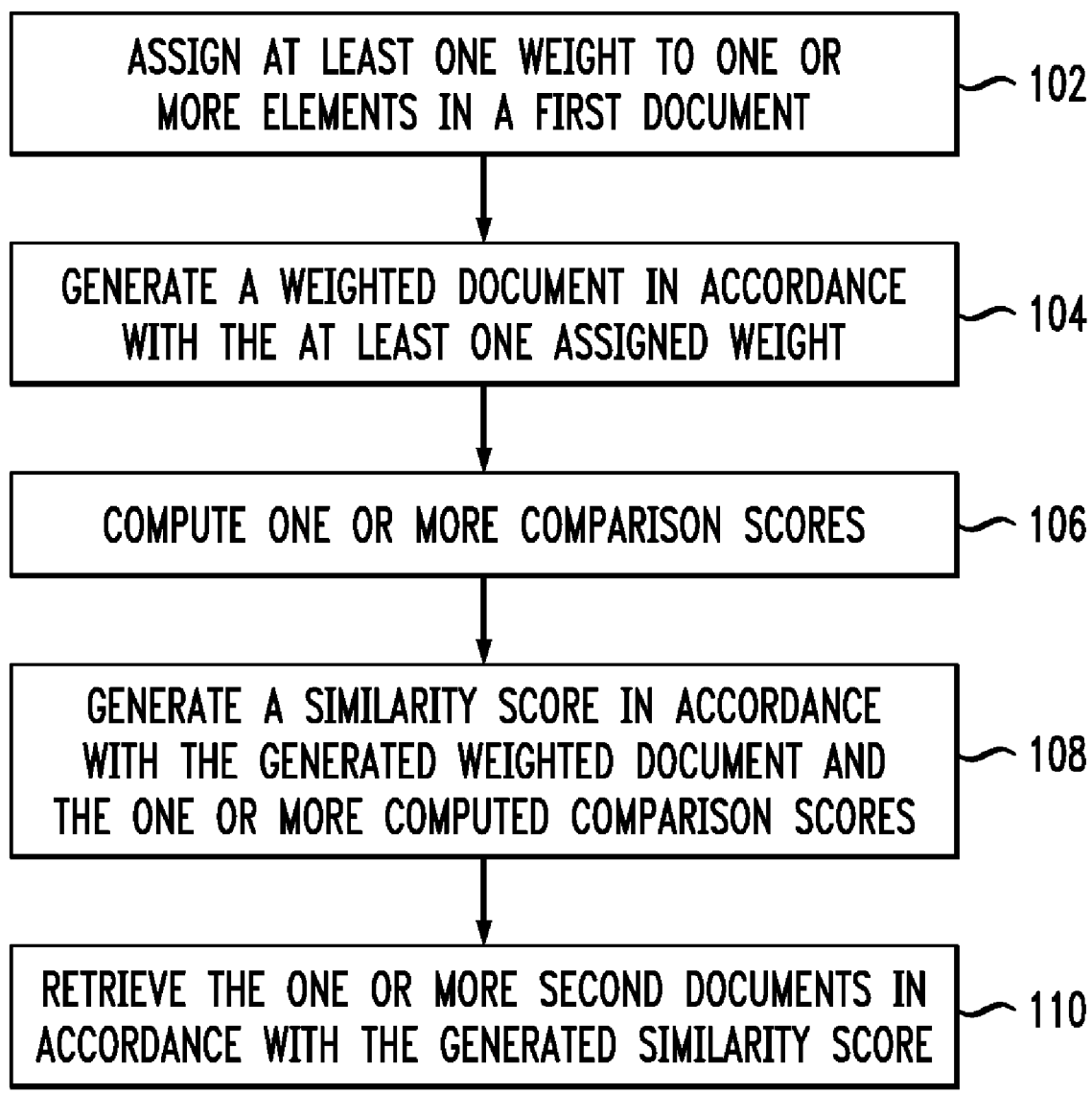
FIG. 1 is a flow diagram illustrating an exemplary methodology for comparing a first document to one or more second documents, according to an embodiment of the present invention.

Referring initially to FIG. 1, a flow diagram illustrates an exemplary methodology for comparing a first document to one or more second documents, according to an embodiment of the present invention. Methodology 100 may be carried out by a computer-based device such as a server. Methodology 100 begins at step 102, where at least one weight is assigned to one or more elements in a first document. In an exemplary embodiment, the first document is to be compared to one or more second documents. For example, the first document may be a medical record of a medical practitioner's patient and the medical practitioner may be interested in retrieving other medical documents (e.g., case studies, patient records, etc.) from a medical database which are similar and/or related to the medical record of his/her patient.

In one embodiment, the medical practitioner loads a medical document (i.e., first document) in CDA format onto the server via a user interface. CDA, which is well known to a person having ordinary skill in the art, is a standard specification promoted by HL7, an American National Standards Institute (ANSI)-accredited standards developing organization. CDA standardizes the representation of various types of clinical documentation and is currently implemented using XML. After introducing the first document, the medical practitioner may then assign weights to the various elements of the document. The weights may be used to define which portions (e.g., elements) of the first document the practitioner believes are important to his/her comparison search. In a CDA document, an element may be a general section, for instance, "Past Medical History," "Medications," and "Allergies and Adverse Reactions," or a simple element such as "Birth Time," "Body Weight Measure," and "Systolic Blood Pressure." An element may comprise one or more attributes (e.g., sub-items), for example, the element "Medication" may include a list of specific drug names. It should be noted that a user may assign weights to one or more elements and/or one or more attributes of a document.

The assigned weights define the comparison strategy to be used when comparing the first document to one or more second documents (e.g., a database of documents). For example, the above-described medical practitioner may be interested in retrieving medical documents for any patients with the same disease and physical background (e.g., age, race, weight, etc.) as his/her patient. Further, of those patients, the practitioner may be interested only in those patients taking the same combination of prescription medications as his/her patient. In an exemplary embodiment, an assigned weight may be any non-negative number that relays a level of importance. For instance, the importance of an element and/or attribute may be defined using a scale from zero to one-hundred; where zero represents a low importance and one-hundred represents a high importance. In the alternative, a scale from zero to one may be utilized; where zero represents a low importance and one represents a high importance. It should be noted that any type of scale may be used and the present invention is not limited to the embodiments described herein. Further, any un-weighted portions of the first document may be given a weight of zero and may be disregarded during any comparison operation.

After weights are assigned by the user, the server may generate a weighted document template in accordance with the user assigned weights (step 104). In an exemplary embodiment, the weighted document is in a standard format that correlates with a standard format of the one or more second documents. In the medical example described above, the standard format is CDA and the generated document is a weighted CDA template.

At step 106, one or more comparison scores are computed. Comparison scores may represent the similarity between one or more elements and/or attributes of a first document and one or more elements and/or attributes of a second document. Comparison scores may be systematically computed using a bottom-up method (e.g., attributes are compared before elements) or a top-down method (e.g., elements are compared before attributes). However, it should be appreciated any comparison method may be applied and the present invention is not limited to these two comparison methods. In an exemplary embodiment, the comparison of specific elements and/or attributes may be carried out by secondary servers and/or systems. For example, elements and attributes may fall under two general categories: numbers and text. The comparison of numbers may involve a simple numerical comparison, e.g., "120" is equal to "120." However, in practice a user may not want to disregard documents that do not have the same exact numerical values. In a preferred embodiment, the user may define one or more similarity ranges for specific elements and/or attributes during the weighting process described above. A similarity range defines a range in which two terms will still be considered similar. For instance, a medical practitioner may be interested in any patients with a systolic arterial pressure +/−20 millimeter of mercury (mmHg) of his/her patient. If the practitioner's patient has a systolic arterial pressure of 120 mmHg, any patients with a systolic arterial pressure between 100 and 140 may be considered similar to the practitioner's patient even though those patients do not have a systolic arterial pressure that is exactly "120." It should be noted that numerical comparisons may be carried out by the server carrying out methodology 100 or the numerical comparisons may be carried out by secondary servers and/or systems.

Similar to the basic comparison of numerical values, the comparison of text may involve a simple text string comparison, e.g., "Hepatitis" is equal to "Hepatitis." However, as discussed above, document preparers may use different terms to describe the same subject. As a result, substantively similar documents may not be recognized during comparison. In an exemplary embodiment, the server carrying out methodology 100 may direct the task of text comparison to one or more language hierarchies. The one or more language hierarchies may be used to compare terms of a specific topic. For example, advanced medical terminology may be mapped out on publicly available language hierarchy systems which elaborate on the definitions and synonyms of medical terms. In addition, some language hierarchy systems may further elaborate on the conceptual relationships between certain terms (e.g., a description of a particular rash may correlate with a specific disease, etc.). In the medical example described above, one of the one or more language hierarchies may be the Unified Medical Language System (UMLS). Systems such as UMLS may return a score representing the similarity/relationship between two inputted terms. If a system is not configured to return a score, the server carrying out methodology 100 may convert the data from the one or more language hierarchies into a comparison score. For example, a short hierarchal distance between two terms in a language hierarchy may reflect a strong level of similarity between two terms; therefore, a high comparison score may be awarded. In contrast, if the hierarchal distance between two terms is large, a low comparison score may be awarded.

It should be noted that the computation of one or more comparison scores may be in accordance with one or more comparison rules. For instance, the one or more comparison rules may determine if an element and/or attribute should be compared using similarity thresholds (e.g., numbers) or language hierarchies (e.g., text). Therefore, depending on the content of the element and/or attribute and the comparison rules, the server carrying out methodology 100 may directly handle a specific comparison or delegate the comparison task to one or more secondary servers and/or systems.

At step 108, a similarity score is generated. The similarity score may summarize the similarity between a first document and a second document. In an illustrative embodiment, each computed comparison score is weighted in accordance with the weighted document template. This may be carried out by multiplying each comparison score to its corresponding weight. The calculated products are then added together, resulting in a final similarity score. The final similarity score reflects the overall similarity between two compared documents. The similarity score may be directly related to the number of similarities between two documents in elements and/or attributes of high importance.

At step 110, the compared document (i.e., a second document) may be retrieved and presented to the user in accordance with its generated similarity score. In one example, the retrieval may depend on a similarity score threshold, for example, the user may only want documents that have a similarity score of 80 or greater. In the alternative, document retrieval may depend on a maximum output number. For instance, the user may only want the first ten documents with the highest similarity scores.

Figure 2:
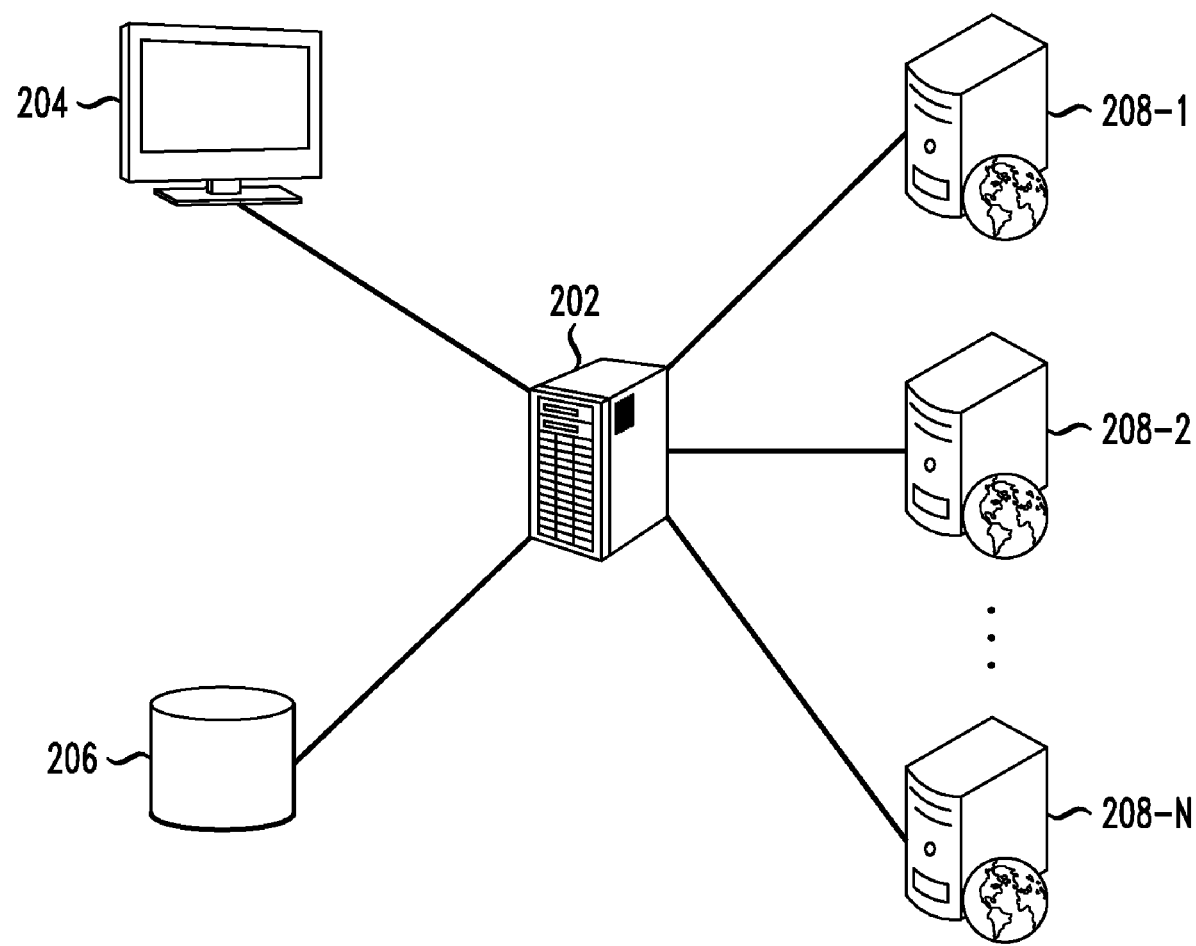
FIG. 2 is a diagram illustrating an exemplary system for carrying out the methodology of FIG. 1, according to an embodiment of the present invention.

Referring now to FIG. 2, a diagram illustrates an exemplary system for carrying out the methodology of FIG. 1, according to an embodiment of the present invention. In FIG. 2, a computer-based device, server 202, carries out methodology 100 of FIG. 1. Server 202 may be coupled to a user interface 204, which may be used by a user to carry out step 102 of FIG. 1. In an exemplary embodiment, a user via user interface 204 loads and assigns weights to a first document. It should be noted that the user may also specify one or more similarity ranges for one or more elements and/or attributes of the first document. After one or more elements and/or attributes of the first document are weighted, the server 202 generates a weighted document template in accordance with the user defined weights (step 104 of FIG. 1). The server 202 then compares the one or more elements and/or attributes of the first document to one or more corresponding elements and/or attributes of one or more second documents stored on a data repository 206 (e.g., a database). Depending on the type of comparison (e.g., text comparison or numerical comparison), the server 202 may compute one or more comparison scores (step 106 of FIG. 1) with the assistance of one or more secondary servers 208-1, . . . , 208-N. The one or more secondary server 208-1, . . . , 208-N, may comprise one or more language hierarchy systems for terminology comparisons.

The one or more comparison scores are then processed by the server 202. As described with reference to step 108 of FIG. 1, the server 202 may generate a similarity score for each compared second document. The similarity score is calculated in accordance with the computed comparison scores and the weighted document template. The similarity score may indicate how similar a second document is to the first document. In an exemplary embodiment, a list of compared documents with corresponding similarity scores is presented to the user via the user interface 204. As described above with reference to step 110 of FIG. 1, the list may be outputted in accordance with a similarity score threshold and/or a maximum output number.

Figure 3:
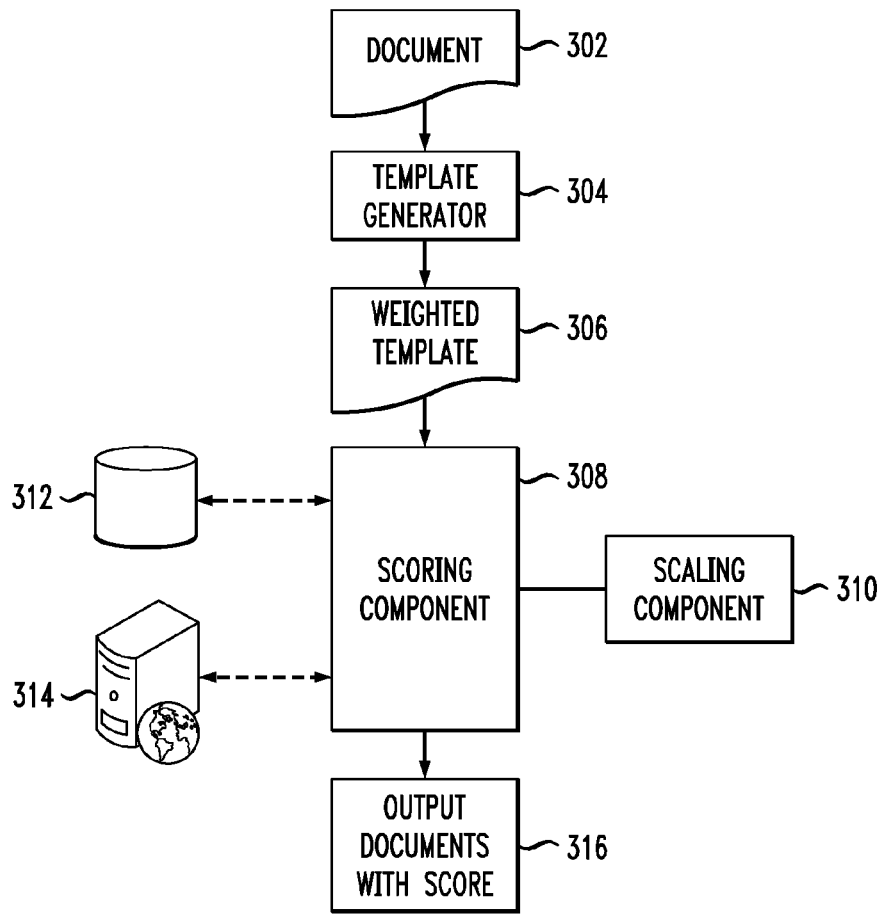
FIG. 3 is a flow diagram illustrating exemplary components, which may be used to carry out the methodology of FIG. 1, according to an embodiment of the present invention.

Referring now to FIG. 3, a flow diagram illustrates exemplary components, which may be used to carry out the methodology of FIG. 1, according to an embodiment of the present invention. The exemplary components of FIG. 3 may be components of server 202 of FIG. 2. Flow 300 begins with a document 302. In an exemplary embodiment, the document 302 is a patient document provided by a medical practitioner. The medical practitioner, who may be interested in searching for case studies related to the treatment of his/her patient, may specify which of the one or more elements and/or attributes of the patient document are important to the practitioner's search. The medical practitioner may specify importance by assigning weights to the one or more elements and/or attributes of the patient document. The medical practitioner may further define similarity ranges, which specify an allowable range in which two compared terms may still be considered similar. Similarity ranges may be used for numerical comparisons (e.g., 120+/−5 mmHg). For instance, the medical practitioner may decide that two compared height values should be considered similar if they are within +/−1 inch.

In accordance with the one or more assigned weights defined by the user, a template generator 304 may generate a weighted template 306. The weighted template 306 may be used by a scoring component 308 to calculate a similarity score. The similarity score represents the similarity between two documents. In an illustrative medical example, the scoring component 308 obtains a second document from a medical repository or database 312. The elements and/or attributes of the first document may then be compared to the elements and/or attributes of the second document. Depending on the term being compared (e.g., numbers or text), the scoring component 308, in accordance with one or more comparison rules, may route comparison tasks to one or more secondary servers 314, which may comprise one or more language hierarchies. In an exemplary embodiment, text-based comparisons involving advanced technical terminology may be routed to the one or more secondary server 314. In the alternative, basic numerical-based comparisons may be handled by the scoring component 308.

In a preferred embodiment, the scoring component 308 may operate concurrently with a scaling component 310. The scaling component 310 may normalize computed comparison scores and ensure that the comparison scores between elements and/or attributes are comparable. For example, in a medical document, the height of an adult may be given in centimeters (cm), and an adult's height may range between the values of 100 cm and 220 cm. Two heights may be considered similar if the heights are within a difference of 5 cm. In another example, a blood calcium level may be given in milligrams per deciliter (mg/dl) and an adult may have a calcium level between 8 mg/dl to 11 mg/dl. Two calcium levels may be considered similar if the two values are within 1 mg/dl. Now, consider two patients, A and B. Patient A has a height of 180 cm and a calcium level of 8.5 mg/dl. Patient B has a height of 185 cm and a calcium level of 10 mg/dl. The difference in height between patient A and patient B is 5 cm, which may be considered similar, and the difference in calcium levels between the two patients is 1.5 mg/dl, which may be considered dissimilar. However, the value difference in height is 5 units and the value difference in calcium level is 1.5 units. Without scaling, the calcium levels between the two patients may be considered more similar than the patients' heights because a difference of 1.5 units is much smaller than a difference of 5 units.

Scaling may be used to normalize the proportions of comparison values and the scaling component 310 may normalize the above scenario in one of two ways. In one embodiment, the similarity ranges of document values are normalized to each other. For example, the height range of +/−5 cm and the calcium level range of +/−1 mg/dl may be mathematically rescaled to a uniform measure. In the second embodiment, scaling rules may be set prior to the comparison process which state that a given comparison of two values returns a comparison score within the range of zero and one. For example, in the illustration described above, the comparison of heights 180 cm and 185 cm may result in a scaled comparison score of 0.7 (similar) and the comparison of calcium levels 8.5 mg/dl and 10 mg/dl may return a scaled comparison score of 0.1 (dissimilar).

The scoring component 308 may compute a comparison score for each compared element and/or attribute. Each comparison score may then be multiplied by its corresponding weight, which may be defined by the weighted template 306. Each multiplication results in a weighted comparison score. The weighted comparison scores may then be added together yielding a total similarity score. The similarity score reflects the similarity of two compared documents. In an exemplary embodiment, a high similarity score may mean that the two compared documents are very similar.

In the example of patient A and patient B described above, a similarity score may be calculated as follows. Recall that patient A has a height of 180 cm and a calcium level of 8.5 mg/dl, and Patient B has a height of 185 cm and a calcium level of 10 mg/dl. Further, the comparison score for height, with scaling, is 0.7; $CS_{Height}=0.7$. And, the comparison score for calcium level, with scaling, is 0.1; $CS_{Calcium}=0.1$. Next, assume that the weighted template 306 defines the following user defined weights: $W_{Height}=20$ and $W_{Calcium}=80$, where a weight of 0 represents a low importance and a weight of 100 represents a high importance. The similarity score between patient A and patient B ($S_{AB}$) may be: $S_{AB}=(CS_{Height} \times W_{Height})+(CS_{Calcium} \times W_{Calcium})$; $S_{AB}=(0.7 \times 20)+(0.1 \times 80)=22$.

It should be noted that the assigned weight, which reflects importance, strongly influences the final similarity score. For example, if another patient, C, had a grossly dissimilar height in comparison to patient A, but had a similar calcium level, patient C may have a higher similarity score than patient B. Assume that patient C has a height of 200 cm and a calcium level of 9.0 mg/dl. If the comparison scores between patient A and patient C are, $CS_{Height}=0$ and $CS_{Calcium}=0.6$, the similarity score between patient A and patient C ($S_{AC}$) may be: $S_{AC}=(0 \times 20)+(0.6 \times 80)=48$. Therefore, the similarity between patient A and patient C is greater than the similarity between patient A and patient B because the calcium level comparison was more important (e.g., heavily weighted) than the height comparison.

After similarity scores are calculated by the scoring component 308, the compared documents with their respective similarity scores are outputted to the user (316). As described above with reference to step 110 of FIG. 1, documents may be outputted in accordance with a minimum similarity score threshold (e.g., only retrieve documents with a similarity score of 80 or greater) and/or a maximum output number (e.g., only retrieve the N most similar documents).

Figure 4:
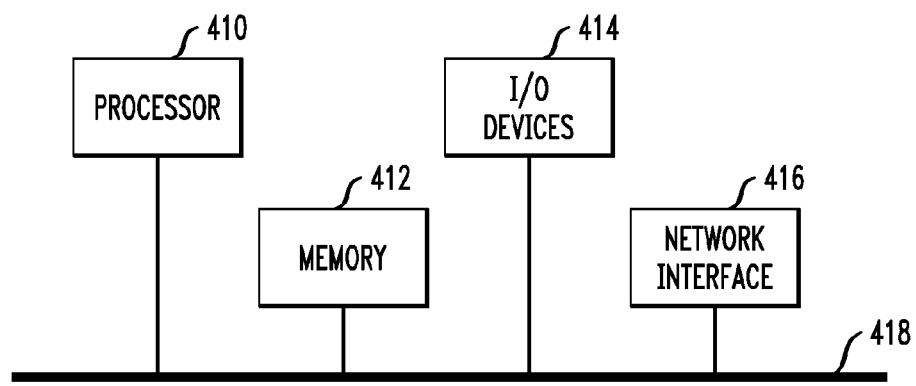
FIG. 4 is a diagram illustrating an illustrative hardware implementation of a computing system in accordance with which one or more components/methodologies of the present invention may be implemented, according to an embodiment of the present invention.

Referring now to FIG. 4, block diagram 400 illustrates an exemplary hardware implementation of a computing system in accordance with which one or more components/methodologies of the invention (e.g., components/methodologies described in the context of FIGS. 1-3) may be implemented, according to an embodiment of the present invention.

As shown, the techniques for comparing a first document to one or more second documents may be implemented in accordance with a processor 410, a memory 412, I/O devices 414, and a network interface 416, coupled via a computer bus 418 or alternate connection arrangement.

It is to be appreciated that the term "processor" as used herein is intended to include any processing device, such as, for example, one that includes a CPU (central processing unit) and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard drive), a removable memory device (e.g., diskette), flash memory, etc. Such memory may be considered a computer-readable storage medium.

In addition, the phrase "input/output devices" or "I/O devices" as used herein is intended to include, for example, one or more input devices (e.g., keyboard, mouse, scanner, etc.) for entering data to the processing unit, and/or one or more output devices (e.g., speaker, display, printer, etc.) for presenting results associated with the processing unit.

Still further, the phrase "network interface" as used herein is intended to include, for example, one or more transceivers to permit the computer system to communicate with another computer system via an appropriate communications protocol.

Software components including instructions or code for performing the methodologies described herein may be stored in one or more of the associated memory devices (e.g., ROM, fixed or removable memory) and, when ready to be utilized, loaded in part or in whole (e.g., into RAM) and executed by a CPU.

As will be appreciated by one skilled in the art, the present invention may be embodied as a system, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, the present invention may take the form of a computer program product embodied in any tangible medium of expression having computer-usable program code embodied in the medium.

Any combination of one or more computer-usable or computer-readable medium(s) may be utilized. The computer-usable or computer-readable medium may be, for example but not limited to, an electronic, magnetic, optical, electromagnetic, infrared, or semiconductor system, apparatus, or device. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or flash memory), an optical fiber, a portable compact disc read-only memory (CD-ROM), an optical storage device, or a magnetic storage device.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Further, the present invention was described above with reference to diagrams of methods, apparatus (systems), and computer program products according to embodiments of the invention. It will be understood that individual functions/acts in the diagrams, and combinations of functions/acts in the diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the diagrams.

These computer program instructions may also be stored in a computer-readable medium that may direct a computer or other programmable data processing apparatus to function in a particular manner, such that the instructions stored in the computer-readable medium produce an article of manufacture including instruction means which implement the functions/acts specified in the diagrams.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the diagrams.

The diagrams illustrate the architecture, functionality, and operation of possible implementations of systems, methods, and computer program products according to various embodiments of the present invention. In this regard, individual functions/acts in the diagrams may represent a module, segment, or portion of code, which comprises one or more executable instructions for implementing the specified logical function(s). It should also be noted that, in some alternative implementations, the functions/acts in the diagrams may occur out of the order noted in the diagrams. For example, two steps shown in succession may, in fact, be executed substantially concurrently, or the steps may sometimes be executed in the reverse order, depending upon the functionality involved. It will also be noted that individual functions/acts in the diagrams, and combinations of functions/acts in the diagrams, may be implemented by special purpose hardware-based systems that perform the specified functions or acts, or combinations of special purpose hardware and computer instructions.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for comparing a first document to one or more second documents, a given document comprising one or more elements and one or more values for each of the one or more elements, the method comprising the steps of:

assigning at least one weight to at least one of the one or more elements in the first document;

generating a weighted template in accordance with the at least one assigned weight;

computing one or more comparison scores for each of the one or more second documents, wherein the one or more comparison scores for a given second document are computed by comparing the one or more values for at least a given element in the first document to one or more values for each of one or more elements in the given second document in accordance with one or more comparison rules, wherein the one or more comparison rules determine at least one technique used for comparing the given element in the first document and a given element in the given second document based on whether the values of the elements being compared are textual or numeric values, wherein the at least one technique determined by the one or more comparison rules comprises using at least one or more language hierarchies to compare textual values; and generating one or more similarity scores for each of the one or more second documents in accordance with the generated weighted template and the one or more computed comparison scores.

2. The method of claim 1, wherein the at least one weight is user defined.

3. The method of claim 1, wherein the weighted template is a Health Level 7 Clinical Document Architecture template.

4. The method of claim 1, wherein at least one of the one or more elements in the first document comprise one or more attributes.

5. The method of claim 4, wherein the one or more elements and the one or more attributes are individually weighted.

6. The method of claim 1, wherein the at least one technique determined by the one or more comparison rules comprises using one or more similarity ranges to compare numerical values.

7. The method of claim 6, wherein the one or more language hierarchies are used to compare terms of a specific topic.

8. The method of claim 7, wherein one of the one or more language hierarchies is a Unified Medical Language System.

9. The method of claim 7, wherein the one or more language hierarchies are configured to return one or more term comparison scores, such that the one or more term comparison scores are used to compute the one or more comparison scores.

10. The method of claim 6, wherein the one or more similarity ranges are used to compare numerical values.

11. The method of claim 1, further comprising the step of retrieving at least one the one or more second documents in accordance with the generated similarity scores.

12. The method of claim 11, wherein the step of retrieving is in accordance with at least one of a similarity score threshold and a maximum output number.

13. The method of claim 1, wherein the at least one technique determined by the one or more comparison rules comprises at least one of scaling and normalizing.

14. The method of claim 1, wherein at least a given term comparison score is based at least in part on a hierarchal distance between the terms in at least a given language hierarchy.

15. The method of claim 1, wherein the weighted template and the one or more second documents are each in accordance with a specified standard format.

16. The method of claim 1, wherein the weighted template is generated such that the at least one weight assigned to the at least one of the one or more elements in the first document is applied to at least one of the one or more elements in each of the one or more second documents.

17. The method of claim 1, wherein the one or more comparison rules further determine which one or more of a plurality of servers are used for comparing the given element in the first document and the given element in the given second document.

18. An apparatus for comparing a first document to one or more second documents, a given document comprising one or more elements and one or more values for each of the one or more elements, the apparatus comprising:
  at least one memory device; and
  at least one processing device coupled to the memory device and operative to: assign at least one weight to at least one of the one or more elements in the first document; generate a weighted template in accordance with the at least one assigned weight; compute one or more comparison scores for each of the one or more second documents, wherein the one or more comparison scores for a given second document are computed by comparing the one or more values for at least a given element in the first document to one or more values for each of one or more elements in the given second document in accordance with one or more comparison rules, wherein the one or more comparison rules determine at least one technique used for comparing the given element in the first document and a given element in the given second document based on whether the values of the elements being compared are textual or numeric values, wherein the at least one technique determined by the one or more comparison rules comprises using at least one or more language hierarchies to compare textual values; and generate one or more similarity scores for each of the one or more second documents in accordance with the generated weighted template and the one or more computed comparison scores.

19. The apparatus of claim 11, wherein the at least one weight is user defined.

20. The apparatus of claim 11, wherein the one or more elements comprise one or more attributes.

21. A system for comparing a first document to one or more second documents, a given document comprising one or more elements and one or more values for each of the one or more elements, the system comprising at least one processing device coupled to at least one memory device and operative to implement:
  an input component for allowing a user to assign at least one weight to at least one of the one or more elements in the first document;
  a template generator for generating a weighted template in accordance with the at least one assigned weight;
  a scoring component for: (i) computing one or more comparison scores for each of the one or more second documents, wherein the one or more comparison scores for a given second document are computed by comparing the one or more values for at least a given element in the first document to one or more values for each of one or more elements in the given second document in accordance with one or more comparison rules, wherein the one or more comparison rules determine at least one technique used for comparing the given element in the first document and a given element in the given second document based on whether the values of the elements being compared are textual or numeric values, wherein the at least one technique determined by the one or more comparison rules comprises using at least one or more language hierarchies to compare textual values; and (ii) generating one or more similarity scores for each of the one or more second documents in accordance with the generated weighted template and the one or more computed comparison scores.

22. A computer-readable storage medium for comparing a first document to one or more second documents, a given document comprising one or more elements and one or more values for each of the one or more elements, the computer-readable storage medium comprising:
  a first program instruction to assign at least one weight to at least one of the one or more elements in the first document;
  a second program instruction to generate a weighted template in accordance with the at least one assigned weight;
  a third program instruction to compute one or more comparison scores by comparing each of the one or more elements in the first document to each of one or more elements in a given second document in accordance with one or more comparison rules, wherein the one or more comparison rules determine at least one technique used for comparing a given element in the first document and a given element in the given second document based on whether the values of the elements being compared are textual or numeric values, wherein the at least one technique determined by the one or more comparison rules comprises using at least one or more language hierarchies to compare textual values;
  a fourth program instruction to generate one or more similarity scores for each of the one or more second documents in accordance with the generated weighted template and the one or more computed comparison scores;
  wherein the first, second, third, and fourth program instructions are stored on the computer-readable storage medium.

* * * * *